United States Patent [19]

Belanger et al.

[11] 4,334,077
[45] Jun. 8, 1982

[54] STEREOSPECIFIC SULFOXIDATION OF DIBENZO THIEPINS

[75] Inventors: Patrice C. Belanger, Dollard des Ormeaux; Joshua Rokach, Chomedey-Laval; Robert N. Young, Senneville; John Scheigetz, Dollard des Ormeaux, all of Canada

[73] Assignee: Merck & Co., Inc., Rahway, N.J.

[21] Appl. No.: 229,223

[22] Filed: Jan. 28, 1981

[51] Int. Cl.³ .................................. C07D 337/14
[52] U.S. Cl. .......................................... 549/12
[58] Field of Search ............................... 549/12

[56] References Cited

U.S. PATENT DOCUMENTS 3,509,154 4/1970 Fouche .................. 549/12
4,104,280 8/1978 Ackrell .................. 549/12
4,237,160 12/1980 Hamel et al. ............ 549/12

OTHER PUBLICATIONS

Chem. Abstracts 91:140734w.

Primary Examiner—Ethel G. Love

Attorney, Agent, or Firm—Hesna J. Pfeiffer; Thomas E. Arther

[57] ABSTRACT

The present invention relates to a process for the preparation of an enantiomer of 7 or 8-fluoro-dibenzo[b,f]-thiepin-3-carboxylic acid having a negative rotation and prostaglandin antagonist activity. The process involves preparation and separation of novel diastereoisomeric esters of 10-hydroxy-7 or 8 fluro-dibenzothiepin-3 carboxylic acid ester followed by stereospecific sulfoxidation of the selected diastereoisomer to produce the corresponding novel sulfoxide having a preponderance of the desired configuration of the sulfoxide entity followed by treatment of the product with a strong base to produce directly the desired (-)7 or 8 fluoro-dibenzo[b,f]thiepin-3 carboxylic acid 5-oxide having the structural formula shown below:

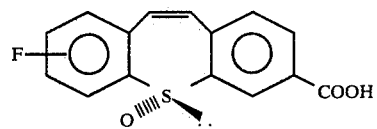

I

3 Claims, No Drawings

STEREOSPECIFIC SULFOXIDATION OF DIBENZO THIEPINS

BACKGROUND OF THE INVENTION

In a prior application, U.S. Ser. No. 210,082 filed Nov. 27, 1980 of Rokach et al., there is disclosed a class of 7 & 8 substituted-dibenzo[b,f]thiepin-3-carboxylic acid as well as the corresponding 5-oxides & 5,5-dioxides. This application discloses, further that certain of these compounds i.e. 7 & 8-fluoro-dibenzo[b,f]thiepin-3-carboxylic-5-oxides exist as racemic mixtures and are resolved into the respective enantiomeric pairs, one enantiomer of which has unusually high activity as a specific antagonist of contractile prostaglandins. Such enantiomers are therefore especially useful in the treatment of asthma, diarrhea, dysmenorrhea, pulmonary hypertension and threatened abortion. The production of such compounds involve fairly complicated syntheses and in order to produce final resolved isomer it is necessary to separate the "active" isomer from the "inactive isomer" with resultant lowered yield of product.

DESCRIPTION OF THE INVENTION

It is an object of the present invention to produce 7 & 8 fluoro-dibenzo[b,f]thiepin-3-carboxylic acid-5-oxides in the following structural configuration;

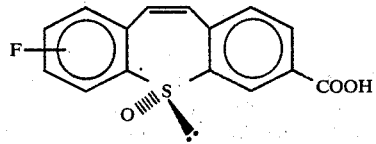

This configuration is established by x-ray crystallographic studies of amide derivatives of the following formula:

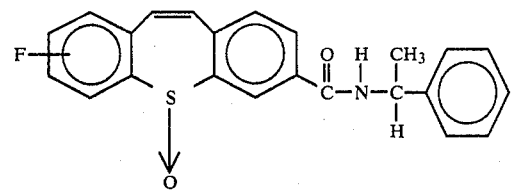

It is a further object of the present invention to produce the desired sulfoxide configuration at an earlier stage of this synthesis, thus avoiding the last step resolution with resultant loss of valuable product.

It has now been found that these and other objects are accomplished by a stereospecific oxidation in which the ring sulfur of the dibenzo-thiepin molecule is oxidized to produce a preponderance of the desired sulfoxide isomer.

In accordance with the present invention an intermediate in the synthesis of 7 or 8 fluoro-dibenzo [b,f]thiepin-3-carboxylic acid-5-oxide is converted by reaction with an optically active acid to a mixture of diastereoisomeric pairs which, after resolution and isolation produces the desired diastereomer. The said diastereoisomer is then oxidized with an organic peroxy carboxylic acid to convert the thiepin to the desired novel thiepin-5-oxide with a preponderance of the desired isomer followed by treatment of said compound with a base to produce the desired exantiomer. This procedure is illustrated in the following flow sheet beginning with 10,11-dihydro-8-fluoro-10-hydroxydibenzo [b,f]thiepin-3-carboxylic acid lower alkyl ester compound III herein below:

FLOW SHEET

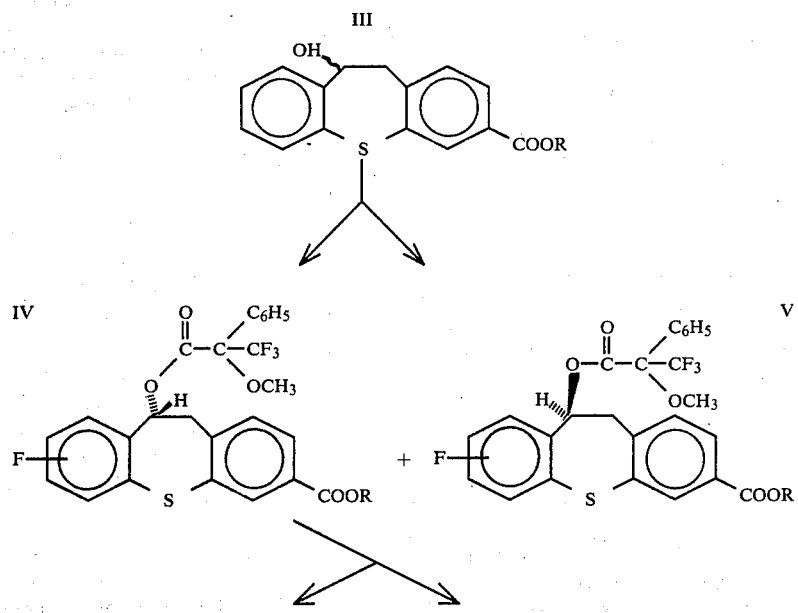

FLOW SHEET
-continued

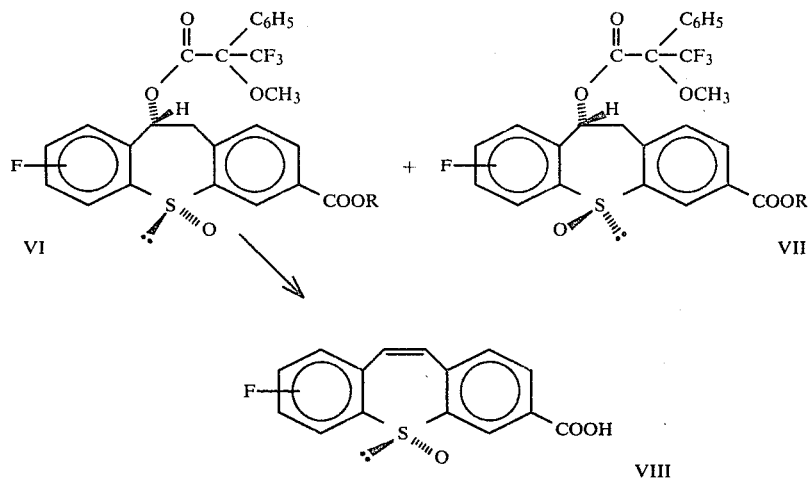

In accordance with the present process compound III hereinabove is reacted with a halide of an optically active carboxylic acid (−) epimer e.g. the acid chloride of (−) α-methoxy-α-trifluoromethyl phenyl acetic acid (Mosher et al.) J. Org. Chem. 34, 2543 (1969) to produce a mixture of diastereomeric esters IV 10-R-((−)-α-methoxy-α-trifluoromethylphenylacetoxy)-8-fluoro-3-carbomethoxydibenzo-[b,f]thiepin and V 10-S-((−)-α-methoxy-α-trifluoromethylphenylacetoxy)8-fluoro-3-carbomethoxydibenzo [b,f]-thiepin. The mixture of diastereoisomeric esters is readily separated using preparative HPLC into two fractions, the preferred ester IV which is the first eluted and the less polar of said isomers and the last eluted and the more polar isomer. The preferred eluting agent is a mixture of a minor amount of ethyl acetate in hexane.

The ester IV is then oxidized with oxidizing agents, preferably peroxy carboxylic acids such as m-chloroperbenzoic acid to produce a novel mixture comprising a major portion of compound VI cis 10-R-((−)-αmethoxy-α-trifluoromethylphenylacetoxy) 8-fluoro-3-carbomethoxydibenzo[b,f]-thiepin-5-oxide and a minor amount of compound VII trans-10-R-((−)-α-methoxy-α-trifluoromethyl phenyl acetoxy)8-fluoro-3-carbomethoxy-dibenzo[b,f]thiepin 5-oxide. This mixture is readily separated by means of preparative TLC (thin layer chromatography) and using as the developing solvent a mixture of ethyl acetate and hexane. Compound VI the less polar of the two components and the first eluted fraction is then treated with a strong base such as an alkali metal hydroxide under hydrolytic conditions to produce directly the desired compound VIII R-(−)8-fluorodibenzo[b,f]thiepin-3-carboxylic acid-5-oxide.

The corresponding 7-fluoro compound i.e. S(−)-7-fluoro-dibenzo[b,f]thiepin-3-carboxylic acid-5-oxide is readily prepared from the corresponding 7-fluoro-10-hydroxy-dibenzo[b,f]thiepin-3-carboxylic acid lower alkyl ester by the same series of reactions and separations.

PREPARATION OF STARTING MATERIAL

Preparation 1

10-Hydroxy-8-fluoro-dibenzo[b,f]thiepin-3-carboxylic acid methyl ester

10-Hydroxy-8-fluoro-dibenzo[b,f]thiepin-3-carboxylic acid (4 g; 13.8 mmoles) dissolved in methanol (100 mL) and treated with excess diazomethane in ether. The volatiles removed under vacuum and the residue, taken up in chloroform, is purified by chromatography in Silica Gel. Elution with 20% ethyl acetate in toluene yielded 3.26 g (78%) of the title compound, m.p. 85°–88° C.

Preparation 2

10-Oxo-8-fluoro-dibenzo[b,f]thiepin-3-carboxylic Acid Methyl Ester

10-Oxo-8-fluoro-dibenzo[b,f]thiepin-3-carboxylic acid (2 g; 6.94 mmoles) is partially dissolved in methanol (20 mL) and is treated with excess diazomethane in ether. The resulting solution is evaporated to dryness, triturated in methanol to yield 1.98 g (94%) of methyl 10-Oxo-8-fluoro-dibenzo [b,f]thiepin-3-carboxylate, m.p. 129°–131° C.

Preparation 3

10-Hydroxy-8-fluoro-dibenzo[b,f]thiepin-3-carboxylic acid methyl ester

10-Oxo-8-fluoro-dibenzo[b,f]thiepin-3-carboxylic acid methyl ester (1.9 g; 6.2 mmoles) was suspended in methanol (25 mL) and sodium borohydride (0.38 g; 10 mmoles) were added. The resulting solution was stirred for 15 minutes. The reaction mixture was then poured into water and extracted with chloroform. The organic phase was then washed with water, dried ($Na_2SO_4$) and concentrated in vacuo to 1.6 g (85%) of an oil that solidified on standing, m.p. 85°–87° C.

This is identical to the compound prepared by the esterification of the 10-hydroxy-8-fluoro-dibenzo[b,f]-thiepin-3-carboxylic acid.

The following examples are illustrative of but not limitative of applicants invention.

EXAMPLE 1

R(1)8-fluorodibenzo[b,f]thiepin-3-carboxylic acid-5-oxide

Step 1—Diastereoisomers of 10-((−)-α-methoxy-α-trifluoromethyl phenyl acetoxy)-8-fluoro-3-carbomethoxy dibenzo[b,f]-thiepin.

To 10-hydroxy-8-fluoro-3-carbomethoxy-dibenzo [b,f]thiepin (733 mg; 2.4 mmoles) dissolved in 10 ml pyridine is added then acid chloride prepared from 1 gm of ((−)-α-methoxy-α-trifluoromethylphenylacetic acid. Mosher et al. 5. Org. Chem. 34, 2543 (1969). The mixture is stirred overnight. It is then poured into water, extracted with chloroform, washed with 1 N HCl, dried (Na$_2$SO$_4$), and concentrated in vacuo to yield a 1.56 gm of crude diastereoisomeric esters. Part of the mixture (700 mg) is separated by preparative HPLC on silica gel (Waters prep 500), using as eluent 5% ethyl acetate in hexane.

The first diastereoisomer 10-R-((−)-α-methoxy-α-trifluoromethylphenylacetoxy)8 fluoro-3-carbomethoxy dibenzo[b,f]thiepin; the less polar isomer that is collected (186 mg) has $\alpha_D^{RT}: +41.5°$ (C=0.5 in CHCl$_3$) whereas the more polar diastereoisomer 10-S-((−)-α-methoxy-α-trifluoromethylphenylacetoxy)8-fluoro-3-carbomethoxy dibenzo[b,f]thiepin, (194 mg) has $\alpha_D^{RT}: -46.9°$(C=0.5 in CHCl$_3$).

Step 2—Oxidation

10-R-((−)-α-methoxy-α-trifluoromethyl-phenylacetoxy)-8-fluoro-3-carbomethoxydibenzo[b,f]-thiepin (less polar isomer), 171 mg. (0.23 mmole) in 15 ml methylene chloride is treated at 0° C. for 45 minutes with m-chloro per benzoic acid (85% pure) 65.0 mg; 0.23 mmole). A small amount of calcium hydroxide is then added and, after stirring the mixture for 10 minutes, filtered and washed with some methylene chloride. The filtrate is concentrated and purified by preparative TLC, developing with 20% ethyl acetate in n-hexane.

The less polar isomer cis-10-R-((−)-α-methoxy-2-trifluoromethylphenylacetoxy)-8-fluoro-3-carbomethoxydibenzo [b,f]thiepin-5-oxide.

(90 mg) has $\alpha_D^{RT}: -87.10$(C=0.5 in CHCl$_3$) and in its mass spectrum, shows a large parent ion at 536 m/e.

The more polar isomer Trans-10-R-((−)-α-methoxy-α-trifluoromethylphenylacetoxy)8-fluoro-3-caromethoxy-dibenzo[b,f]thiepin-5-oxide (15 mg) has $\alpha_D^{RT}= +76.6°$ (C=0.5 in CHCl$_3$) and gives a M+ at 536 m/e.

Step 3

The cis ester $\alpha_D^{RT}= -87.1°$ (40 mg; 0.075 mole) is dissolved in 10 ml methanol and is treated with 0.5 ml 10 N sodium hydroxide at reflux for 30 minutes. The reaction mixture is concentrated in vacuo and the residue is dissolved with the minimum amount of methanol. The resulting solution is acidified with 6 N HCl, diluted with water (10 ml) and the resulting solid is filtered. It is found to be identical to R(−)8-fluoro-dibenzo[b,f]thiepin-5-oxide-3-carboxylic acid prepared by other methods.

The procedure of Example 1 is repeated for Steps 1 & 2 replacing the acid chloride of α-methoxy-α-trifluoromethyl phenyl acetic acid with the corresponding α-methoxyphenylacetyl chloride with production of the following intermediates.

Step 1

10-R-((−)-α-methoxyphenylacetoxy)8-fluoro-3-carbomethoxy dibenzo [b,f]thiepin (less polar isomer) $\alpha_D^{RT}= +9.4°$ C=0.5 in chlorform 10-S((−)-α-methoxy-phenylacetoxy)-8-fluoro-3-carbomethoxy dibenzo [b,f]thiepin (more polar isomer) $\alpha_D= -33.4°$ (C=0.5 in chloroform).

Step 2

Cis-10-R-((−)-α-methoxyphenylacetoxy)-8-fluoro-3-carbomethoxydibenzo[b,f]thiepin (less polar isomer) 175 mg. [d]RT= −33.1° (C=0.5 in chloroform) trans-10-R-((−)-α-methoxyphenylacetoxy)-8-fluoro-3-carbomethoxydibenzo[b,f]thiepin-5-oxide (more polar isomer)

29 mg. $\alpha_D^{RT}= +8.7°$ C=0.5 in chloroform.

What is claimed is:

1. A compound of the formula:

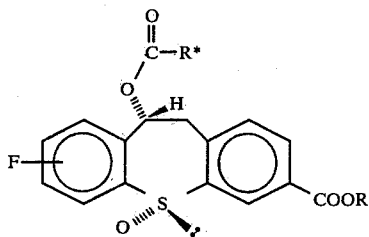

wherein the F substituent is attached to the 7 or 8 carbon; R* is an α-substituted benzyl substituent selected from α-methoxy-α-trifluoromethylbenzyl and α-methoxy benzyl; and R is a lower alkyl substituent.

2. A compound according to claim 1 which comprises cis 10-R-((−)-α-methoxy-α-trifluoro-methylphenylacetoxy)8-fluoro-3-carbomethoxydibenzo [b,f]thiepin-5-oxide.

3. A compound according to claim 1 which comprises cis 10-R-((−)-α-methoxyphenylacetyl) 8-fluoro-3-carbomethoxydibenzo [b,f]thiepin-5-oxide.

* * * * *